US00PP14571P29

(12) United States Plant Patent
Zaiger et al.

(10) Patent No.: US PP14,571 P2
(45) Date of Patent: Mar. 2, 2004

(54) INTERSPECIFIC TREE NAMED 'SPRING FLAVOR'

(50) Latin Name: ***Prunus salicina*×(*Prunus salicina*×*Prunus armeniaca*)×(*Prunus persica*×*Prunus armeniaca*)×*Prunus armeniaca***
Varietal Denomination: Spring Flavor

(76) Inventors: Gary Neil Zaiger, 1907 Elm Ave., Modesto, CA (US) 95358; Grant Gene Zaiger, 4005 California Ave., Modesta, CA (US) 95358; Leith Marie Gardner, 1207 Grimes Ave., Modesto, CA (US) 95358

( * ) Notice: Subject to any disclaimer, the term of this patent is extended or adjusted under 35 U.S.C. 154(b) by 21 days.

(21) Appl. No.: 10/318,679

(22) Filed: Dec. 16, 2002

(51) Int. Cl.[7] ..... A01H 5/00
(52) U.S. Cl. ..... Plt./180

(58) Field of Search ..... Plt./180

*Primary Examiner*—Bruce R. Campell
*Assistant Examiner*—Anne Marie Grunberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calf., with standard commercial fruit growing practices, such as pruning, thinning, spraying, irrigation and fertilization. Its novelty consist of the following combination of desirable features:

1. Large size fruit maturing in the early season.
2. Fruit with excellent flavor and eating quality.
3. The tree with a vigorous, upright growth habit.
4. Fruit with a good balance between sugar and acid.
5. Fruit with good storage and handling quality.
6. Heavy and regular bearing of fruit.
7. Fruit with an attractive, reddish maroon color.

1 Drawing Sheet

Genus and species: [*Prunus salicina*×(*Prunus salicina*×*Prunus armeniaca*)×(*Prunus persica*×*Prunus armeniaca*)×*Prunus armeniaca*].

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this backgroud of our activities that the present variety of interspecific tree was originated and asexually reproduced by us in our experimental orchard located near Modesto, Stanislaus County, Calif.

PRIOR VARIETIES

Among the existing varieties of plum apricot and interspecific trees, which are known to us, and mentioned herein, 'Mariposa' Plum (U.S. Pat. No. 111), 'Red Beaut' Plum (U.S. Plant Pat. No. 2,539), 'Modesto' Apricot (U.S. Plant Pat. No. 2,543) and 'Geo Pride' Interspecific (U.S. Plant Pat. No. 10,386).

STATEMENT REGARDING FEDERALLY SPONSORED RESEARCH AND DEVELOPMENT

Not applicable.

ORIGIN OF THE VARIETY

The new and distinct interspecific tree was originated by us from crosses of the following species, *Prunus salicina, Prunus armeniaca* and *Prunus persica*. The present new variety was selected from a first generation cross between two proprietary parents with field identification numbers 288LF477 and 391LD449. The maternal parent (288LF477) originated from a cross of 'Geo Pride' Interspecific (U.S. Plant Pat. No. 10,386) with a proprietary interspecific parent, originating from crosses of the following species *Prunus salicina, Prunus armeniaca* and *Prunus persica*. The paternal parent (391LD449) originated as an interspecific selection from crosses of the following; 'Modesto' Apricot (U.S. Plant Pat. No. 2,543), proprietary plumcot (4G1180), and an apricot of unknown parentage. A large number of these first generation seedlings growing on their own root system were budded to trees of 'Nemaguard' Rootstock (non-patented) and under close and careful observation, one such budded tree exhibited desirable, early maturing fruit characteristics and was selected for additional asexual propagation and commercialization.

ASEXUAL REPRODUCTION OF THE VARIETY

Asexual reproduction of the new and distinct variety of interspecific tree was by budding, in 1998, to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new interspecific tree originated from crosses of the following species, (Plum×Plumcot×Peachcot×

Apricot), [*Prunus salicina*×(*Prunus salicina*×*Prunus armeniaca*)×(*Prunus persica*×*Prunus armeniaca*)×*Prunus armeniaca*] is of large size, vigorous, upright growth and a regular and productive bearer of large, yellow flesh fruit with excellent flavor and eating quality. The fruit is further characterized by having firm flesh, good shipping and handling quality, being relatively uniform in size throughout the tree and maturing in the early maturity season. In comparision to the fruit of the early maturing parent 'Red Beaut' Plum (U.S. Plant Pat. No. 2,539), the fruit of the present variety is larger in size with heavier production and is 7 days earlier in maturity. In comparison to the fruit of the interspecfic tree 'Geo Pride' (U.S. Plant Pat. No. 10,386), the fruit of the new variety is larger in size and is approximately 50 days earlier in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 5 year old specimens grown near Modesto, Calif., with color in accordance with Munsell Book of Color.

Tree:

*Size.*—Large. Pruned to 3 to 3.5 meters in height and width, primarily for econmical harvesting of fruit.

*Vigor.*—Vigorous. Growth of 1.5 to 2 meters the first growing season, varies with fertility, type of soil and climatic conditions.

*Growth.*—Upright, similar to standard plum trees.

*Branching Habit.*—Upright, crotch angle approximately 30°, increase with heavy production.

*Productivity.*—Heavy, sets from 1½ to several times more fruit than is desired, thinning and spacing of fruit necessary.

*Bearer.*—Regular. Adequate fruit set 3 consecutive years. No alternate bearing observed.

*Fertility.*—Self-sterile, pollenizer required.

*Density.*—Medium dense. Usually pruned to vase shape to allow more sunlight to center of tree to enhance fruit color and health of fruit spurs.

*Hardiness.*—Hardy in all stone fruit growing areas of California. Winter chilling requirement approximately 450 to 500 hours at or below 45° F.

Trunk:

*Size.*—Medium to large. Average circumference 48.3 cm at 27.9 cm from ground on a 5 year old tree.

*Texture.*—Medium shaggy, becomes rougher with age.

*Color.*—Varies from 5YR 5/2 to 7.5YR 3/2.

Branches:

*Size.*—Medium. Average circumference 12.9 cm at 0.8 meter from ground. Crotch angle approximately 30°, increases with heavy crop load.

*Surface texture.*—New growth smooth. Mature growth moderately rough.

*Lenticels.*—Average number of 34 in a 25.8 square cm section. Average length 3.6 mm. Average width 1.4 mm. Color varies from 2.5YR 5/10 to 5YR 5/10.

*Color.*—New growth varies from 7.5YR 6/2 to 7.5YR 4/2, varies with exposure to sunlight. Old growth varies from 2.5YR 3/2 to 5YR 4/2, varies with age or growth.

Leaves:

*Size.*—Small to medium. Average length 93.8 mm. Average width 42.8 mm.

*Form.*—Oblanceolate.

*Apex.*—Acuminate.

*Base.*—Cuneate.

*Margin.*—Doubly serrate.

*Thickness.*—Medium.

*Surface texture.*—Upper surface relatively smooth, slight indentations over midrib and leaf veins, glabrous. Lower surface relatively smooth except for small ridges created by midrib and pinnate venation, glabrous.

*Petiole.*—Average length 14.5 mm. Average width 1.6 mm. Color varies from 2.5GY 6/6 to 10R 4/8, varies with exposure to sunlight. Grooved longitudinally.

*Glands.*—Reniform. Medium to large. Average length 0.9 mm. Average diameter 0.6 mm. Number varies from 3 to 6, average 4. Located on upper portion of petiole and lower portion of leaf blade. Color varies from 2.5GY 6/4 to 5GY 7/4.

*Color.*—Upper surface varies from 2.5GY 5/8 to 5GY 4/6. Lower surface varies from 2.5GY 5/4 to 5GY 5/4. Midvein color varies from 2.5GY 8/6 to 5GY 6/4.

Flower buds:

*Size.*—Medium to large. Average length 8.9 mm. Average diameter 5.2 mm.

*Form.*—Conical, becoming elongated before opening.

*Hardiness.*—Hardy in all stone fruit growing areas of California. Grown in USDA Hardiness Zone 9 near Modesto, Calif.

*Pubescence.*—Glabrous.

*Color.*—N 9.5/.

*Pedicel.*—Medium. Average length 8.3 mm. Average width 0.8 mm. Color 5GY 6/7.

*Number of buds per spur.*—Varies from 2 to 10, average 6.

Flowers:

*Size.*—Large. Average height 12.6 mm. Average diameter 17.7 mm.

*Petals.*—Number 5, alternately arranged to sepals. Ovate shape. Average length 11.2 mm. Average width 9.1 mm. Color N 9.5/. Margin — entire, slightly cupped near apex.

*Sepals.*—Number 5, alternately arranged to petals. Shape — triangular, both upper and lower surfaces glabrous. Average length 4.3 mm. Average width 2.9 mm. Color — upper surface 5GY 7/12. Lower surface 5GY 6/10.

*Stamens.*—Average number per flower 31. Average filament length 8.9 mm. Filament color N 9.5/. Color of anthers 3.75Y 8/14.

*Pollen.*—Self sterile, pollenizer required. Color 3.75Y 8/14.

*Pistil.*—Normally 1, varies from 1 to 2. Average length 10.5 mm. Color 2.5GY 8/6. Surface — glabrous.

*Aroma*. Very slight.

*Blooming period*.—Date of First Bloom Feb. 16, 2002. Date of Petal Fall Feb. 25, 2002. Varies slightly with climatic conditions.

*Color*.—N 9.5/.

*Number flowers per flower bud*.—Usually 2, varies from 1 to 3.

*Pedicel*.—Medium. Average length 9.8 mm. Average width 0.9 mm. Color 2.5GY 8/8.

Fruit:

*Maturity when described*.—Firm ripe.

*Date of first picking*.—May 22, 2002.

*Date of last picking*.—May 28, 2002, varies slightly with climatic conditions.

*Size*.—Large. Average diameter axially 50.9 mm. Average transversely in suture plane 58.8 mm. Average weight 119.3 grams, varies slightly with fertility of the soil, amount of thinning and climatic conditions.

*Form*.—Globose, slightly flattened at apex and base.

*Suture*.—Very shallow, extends from base to apex.

*Ventral surface*.—Nearly rounded, very slightly flattened.

*Apex*.—Varies from slightly flattened to slightly retuse.

*Base*.—Retuse.

*Cavity*.—Rounded to slightly elongated in suture plane. Average depth 4.2 mm. Average diameter 8.1 mm.

Stem:

*Size*.—Large. Average length 17.8 mm. Average diameter 2.5 mm.

*Color*.—Varies from 10Y 6/6 to 10Y 5/4.

Flesh:

*Ripens*.—Relatively even, slightly earlier near apex.

*Texture*.—Firm.

*Fibers*.—Few, small, tender.

*Firmess*.—Firm, comparable to 'Red Beaut' Plum (U.S. Plant Pat. No. 2,539).

*Aroma*.—Moderate.

*Amydgalin*.—Undetected.

*Eating quality*.—Excellent.

*Flavor*.—Excellent, mild, sweet.

*Juice*.—Moderately juicy, enhances flavor.

*Brix*.—Average 11.6°, good balance between acid and sugar, varies slightly with amount of fruit per tree and climatic conditions.

*Color*.—Varies from 2.5Y 8/4 to 2.5Y 8/6, slight bleeding of 2.5R 5/8 from skin toward pit cavity. Pit cavity varies from 2.5Y 7/6 to 2.5Y 6/10.

Skin:

*Thickness*.—Medium.

*Surface*.—Smooth.

*Bloom*.—Moderate amount, complete coverage.

*Tendency to crack*.—None.

*Color*.—Ground cover varies from 2.5Y 8.5/6 to 2.5Y 8/6. Overspread with 2.5R 2/8 to 5R 3/10. Very small, randomly spaced areas of ground color exposed to skin surface, creating a speckled pattern to skin in some areas.

*Tenacity*.—Tenacious to flesh.

*Astringency*.—Undetected.

Stone:

*Type*.—Clingstone.

*Size*.—Average length 22.7 mm. Average width 20.1 mm. Average depth 10.0 mm.

*Form*.—Obovate.

*Base*.—Varies from flat to slightly rounded.

*Apex*.—Relatively rounded, no point.

*Surface*.—Very lightly pitted throughout. Usually 3 to 4 narrow ridges of various lengths extending from base toward apex. One shallow groove on each side of suture.

*Sides*.—Equal.

*Tendency to split*.—None.

*Color*.—Varies from 7.5YR 7/8 to 7.5YR 7/10 when dry.

Kernal:

*Form*.—Ovate.

*Taste*.—Bitter.

*Viability*.—Poor viability, embryo only partially developed.

*Size*.—Average length 11.6 mm. Average width 10.1 mm. Average depth 6.1 mm.

*Skin color*.—5Y 9/4 when dry.

Use: Dessert. Market — local and long distance.

Keeping quality: Good, held firm for 10 days in cold storage at 38° to 42° F. without internal breakdown or appreciable loss of flavor.

Shipping quality: Good, showed minimal skin scarring or flesh bruising of fruit in picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, virogous, upright growth and regular and productive bearer of large, early maturing, yellow flesh fruit with excellent flavor and eating quality; in comparison to the early maturing fruit of 'Red Beaut' Plum (U.S. Plant Pat. No. 2,539), the fruit of the present new variety is larger in size and approximately 7 days earlier in maturity.

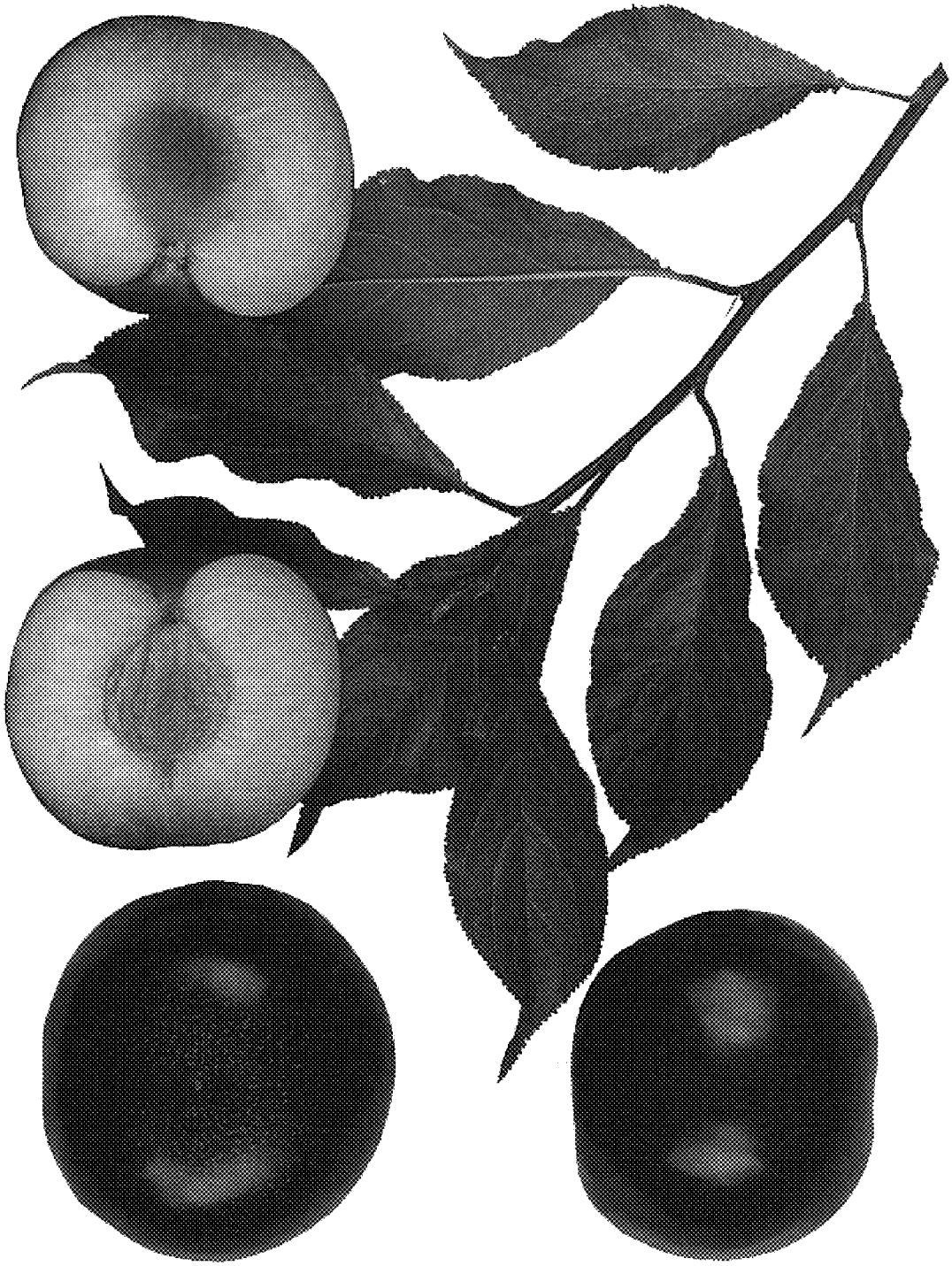

* * * * *